US012745918B2

(12) United States Patent
King, IV et al.

(10) Patent No.: US 12,745,918 B2
(45) Date of Patent: Sep. 29, 2026

(54) METHOD, SYSTEM AND DEVICE FOR INDIVIDUALIZED SUPPLEMENTAL OXYGEN THERAPY FOR PRETERM INFANTS

(71) Applicant: Medical Predictive Science Corporation, Charlottesville, VA (US)

(72) Inventors: William E. King, IV, North Garden, VA (US); Urvi Jhaveri Sanghvi, Centennial, CO (US)

(73) Assignee: Medical Predictive Science Corporation

( * ) Notice: Subject to any disclaimer, the term of this patent is extended or adjusted under 35 U.S.C. 154(b) by 641 days.

(21) Appl. No.: 18/140,973

(22) Filed: Apr. 28, 2023

(65) Prior Publication Data

US 2023/0397829 A1 Dec. 14, 2023

Related U.S. Application Data

(60) Provisional application No. 63/351,706, filed on Jun. 13, 2022.

(51) Int. Cl.

*A61B 5/00* (2006.01)
*A61B 5/0205* (2006.01)
*A61B 5/024* (2006.01)

(52) U.S. Cl.

CPC ........ *A61B 5/02405* (2013.01); *A61B 5/0205* (2013.01); *A61M 2202/0208* (2013.01)

(58) Field of Classification Search

CPC ..... A61B 5/02405; A61B 5/0205; A61B 5/08; A61B 2503/045; A61M 16/1005;

(Continued)

(56) References Cited

U.S. PATENT DOCUMENTS 4,889,116 A * 12/1989 Taube ................... A61M 16/00 128/204.23
6,216,032 B1 * 4/2001 Griffin ............... A61B 5/02405 600/515

(Continued)

FOREIGN PATENT DOCUMENTS

CN 113693556 A 11/2021
JP 2011-516538 A 5/2011

(Continued)

OTHER PUBLICATIONS

Afolayan et al.; Call for Papers Biomarkers in lung diseases: from Pathogenesis to Prediction to New Therapies, “Decreased endothelial nitric oxide synthase expression and function contribute to impared mitochondrial biogenesis ans oxidative stress in fetal lambs with persistent pulmonary hypertension” 310:L40-L49, Oct. 30, 2015.

(Continued)

*Primary Examiner* — Margaret M Luarca
*Assistant Examiner* — Sarah B Lederer
(74) *Attorney, Agent, or Firm* — Williams Mullen; Thomas F. Bergert

(57) ABSTRACT

Embodiments of a method, system and/or device assist in dynamically optimizing preterm infants' oxygen saturation target range in a manner that is individualized to the infants' physiological state. In exemplary embodiments, oxygen saturation is dynamically targeted by monitoring the heart rate to determine a heart rate variability measurement and/or determining a pulmonary resilience measurement (PRM) in a preterm infant and adjusting an oxygen saturation target range for the preterm infant. In various embodiments, the heart rate variability measurement and/or PRM is evaluated against a pre-established threshold, and if the heart rate variability measurement and/or PRM meets or exceeds the pre-established threshold, the oxygen saturation target range is adjusted. Embodiments of the present disclosure can (Continued)

further optionally re-adjust the oxygen saturation target range at regular time intervals based on the heart rate variability measurement and/or PRM.

26 Claims, 4 Drawing Sheets

(58) Field of Classification Search
CPC .............. A61M 16/024; A61M 16/026; A61M 16/0051; A61M 2202/0208; A61M 2205/3334
See application file for complete search history.

(56) References Cited

U.S. PATENT DOCUMENTS

| | | | | |
|---|---|---|---|---|
| 9,730,645 | B2 | 8/2017 | Mcgregor et al. | |
| 2011/0067697 | A1 | 3/2011 | Lellouche et al. | |
| 2011/0190611 | A1 | 8/2011 | Rabi | |
| 2017/0231568 | A1 | 8/2017 | An et al. | |
| 2018/0070886 | A1 | 3/2018 | Fairchild et al. | |
| 2019/0117149 | A1* | 4/2019 | Gouda | A61B 5/486 |
| 2019/0320974 | A1* | 10/2019 | Alzamzmi | A61B 5/746 |
| 2019/0321574 | A1* | 10/2019 | Sallee | A61M 16/024 |
| 2019/0365281 | A1* | 12/2019 | Orr | A61B 5/0836 |

FOREIGN PATENT DOCUMENTS

| | | | |
|---|---|---|---|
| JP | 2016-512777 | A | 5/2016 |
| JP | 2021-530276 | A | 11/2021 |
| KR | 101592123 | | 4/2016 |
| KR | 10-2019-0008426 | A | 1/2019 |
| WO | 2016049780 | | 4/2016 |
| WO | 2022/046686 | A1 | 3/2022 |

OTHER PUBLICATIONS

Aghili et al.; The American Physical Society, "Scaling and Ordering of Neonatal Heart Rate Variability"; vol. 74, No. 7, Feb. 13, 1995.
Al-Ghanem et al., Journal of Perinatology, "Bronchopulmonary dysplasia and pulmonary hypertension: a meta-analysis", vol. 37, pp. 414-419, Jan. 12, 2017.
Alonzo et al., Journal of National-Perinatal Medicine, "Dexamethasone effect on heart rate variability in preterm infants on mechanical ventilation", vol. 10, pp. 425-430, Jun. 2, 2017.
Al-Shargabi et al., American Journal of Perinatology,"Changes in Autonomic Tone in Premature Infants Developing Necrotizing Enterocolitis", vol. 35, pp. 1079-1086, Apr. 2, 2018.
Alvira et al., The Journal of Pediatrics, "Can We Understand the Pathobiology of Bronchopulmonary Dysplasia", vol. 190, Nov. 2017.
Amess et al., Early Human Developments, "Visual assessment of heart rate variability patterns associated with neonatalinfection in preterm infants", vol. 134, pp. 31-33, (2019).
Aschner et al., J Pediatr. Author manuscript; "Can We Prevent Bronchopulmonary Dysplasia?", vol. 189, pp. 26-30, Oct. 2017.
Askie, et al., Cochrane Library, Effects of targeting lower versus higher arterial oxygen saturations on death or disability in preterm infants (Review), Issue 4, (2017).
Askie et al., JAMA, Association Between Oxygen Saturation Targeting and Death or Disability in Extremely Preterm Infants in the Neonatal Oxygenation Prospective Meta-analysis Collaboration; vol. 319( No. 21) pp. 2190-2201, Jun. 5, 2018.
Balany et al., Frontiers in Medicine, "Understanding the Impact of Infection, Infammation, and Their Persistence in the Pathogenesis of Bronchopulmonary Dysplasia", vol. 2, Article 90, Dec. 21, 2015.
Ballard et al., The New England Journal of Medicine, "Inhaled Nitric Oxide in Preterm Infants Undergoing Mechanical Ventilation", vol. 355 No. 4, Jul. 27, 2006.
Bancalari et al., American Journal of Perinatology, " Respiratory Instability and Hypoxemia Episodesin Preterm Infants", vol. 35 No. 6 pp. 534-536, (2018).
Baron et al., Journal of Personality and Social Psychology, "The Moderator-Mediator Variable Distinction in Social Psychological Research: Conceptual, Strategic and Statistical Considerations", vol. 51, No. 6, pp. 1173-1182, 1986.
Belsky et al., Psychological Bulletin, "Beyond Diathesis Stress: Differential Susceptibility to Environmental Influences", vol. 135 No. 6, pp. 885-908 (2009).
Benaron et al., Arch Pediatr Adolesc Med, "Maximizing the Stability of Oxygen Delivered Via Nasal Cannula", vol. 148, pp. 294-300, Mar. 1994.
Beuchée et al., Neonatology, "Uncorrelated Randomness of the Heart Rate Is Associated with Sepsisin Sick Premature Infants", vol. 96 No.2, pp. 109-114, Mar. 12, 2009.
Blencowe et al., Reproductive Health, "Born Too Soon: The global epidemiology of15 million preterm births", vol. 10 (Suppl 1):S2 (2013).
Bohanon et al., The American Journal of Surgery, "Heart rate variability analysis is more sensitive at identifying neonatal sepsis than conventional vital signs", vol. 210, No. 4, pp. 661-667 (Oct. 2015).
Borovikova et al., Nature, "Vagus nerve stimulation attenuates the systemic in˜ammatoryresponse to endotoxin", vol. 405, May 25, 2000.
Boyce et al., Psychosomatic Medicine, "Psychobiologic Reactivity to Stress and Childhood Respiratory Illness: Results of Two Prospective Studies", vol. 57, pp. 411-422 (1995).
Boyce et al., Development and Psychopathology, "Biological sensitivity to context: I. Anevolutionary-developmental theory of theorigins and functions of stress reactivity", vol. 17, pp. 271-301 (2005).
Buczynski et al., Seminars in Perinatology, "The role of hyperoxia in the pathogenesis of experimental BPD", vol. 37, pp. 69-78 (2013).
Burtchen et al., Early Human Development, Autonomic signatures of late preterm, early term, and full term neonatesduring early postnatal life, vol. 137 (2019).
Carvalho et al., Journal of Immunology Research, "Preterm Neonates with Respiratory Distress Syndrome: Ventilator-Induced Lung Injury and Oxidative Stress" (2018).
Charaborty et al., Paediatrics, "Predicting extubation outcomes usingthe Heart Rate Characteristics indexin preterm infants: a cohort study", May 15, 2020.
Chavan et al., Journal of Immunology, "Essential Neuroscience in Immunology", vol. 198, pp. 3389-3397 (2017).
Chavan et al., Immunity, "Mechanisms and Therapeutic Relevanceof Neuro-immune Communication" (2017).
Chawanpaiboon et al., www.thelancet.com, "Global, regional, and national estimates of levels of pretermbirth in 2014: a systematic review and modelling analysis", Oct. 29, 2018.
Chen et al., American Journal of Obstetrics, "Electronic fetal heart rate monitoring and its relationshipto neonatal and infant mortality in the United States", Jun. 2011.
Chiera et al., Frontiers in Neuroscience, "Heart Rate Variability in the PerinatalPeriod: A Critical and ConceptualReview", vol. 14, Article 564486, Sep. 25, 2020.
Clark et al., Pediatric Research, "Predictive monitoring for respiratory decompensation leading to urgent unplanned intubation in the neonatal intensive care unit", vol. 73, Jan. 2013.
Coggins et al., Arch Dis Child Fetal Neonatal Ed, "Heart rate characteristic index monitoring for bloodstream infection in an NICU: a 3-yearexperience", (2016).
Cohen et al., Pediatric Research, "Fetal-growth-restricted preterm infants display compromised autonomic cardiovascular control on the first postnatal day but not during infancy", vol. 82 No. 3, Sep. 2017.
Costa et al., The American Physical Society, "Multiscale entropy analysis of biological signals", Feb. 18, 2005.
Cummings et al., The American Academy of Pediatrics, "Oxygen Targeting in Extremely Low Birth Weight Infants", vol. 138, No. 2, Aug. 2016.

(56) References Cited

OTHER PUBLICATIONS

Czippelova et al., Biomedical Signal Processing and Control, "Time irreversibility of heart rate oscillations in newborns—Does it reflect system nonlinearity?", (2015).
Czura et al., Journal of Endotoxin Research, "Neural inhibition of inflammation: the cholinergic", vol. 9, No. 6 (2003).
D'Angio et al., J. Pediatr. Author Manuscript, "Blood Cytokine Profiles Associated with Distinct Patterns of Bronchopulmonary Dysplasia among Extremely Low Birth Weight Infants", vol. 174, pp. 45-51, Jul. 2016.
Davidson et al., Journal of Clinical Medicine, "Bronchopulmonary Dysplasia: Chronic Lung Disease of Infancy and Long-Term Pulmonary Outcomes", Jan. 6, 2017.
Dereymaeker et al., Early Human Development, "Review of sleep-EEG in preterm and term neonates", (2017).
De Souza Filho et al., BMC Cardiovascular Disorders, "Evaluation of the autonomic nervous system by analysis of heart rate variability in the preterm infants", vol. 19, p. 198, (2019).
Dietz et al., Am J Reprod Immunol., "Oxidative stress diseases unique to the perinatal period:A window into the developing innate immune response", (2018).
Di Fiore et al., The Journal of Pediatrics, "Low Oxygen Saturation Target Range is Associated with Increased Incidence of Intermittent Hypoxemia", vol. 161, No. 6, (2012).
Di Fiore et al., Journal of Perinatology, "Cardiorespiratory events in preterm infants: etiology and monitoring technologies", vol. 36, pp. 165-171, (2016).
Di Fiore et al., Journal of Perinatology, "Cardiorespiratory events in preterm infants: interventions and consequences", vol. 36, pp. 251-258, (2016).
Ducrocq et al., Biology of the Neonate, "Vasomotor Reactivity in Premature Neonates at Term", vol. 82, No. 1, pp. 9-16, (2002).
Ellis et al., Development and Psychopathology, "Differential susceptibility to the environment:An evolutionary—neurodevelopmental theory", vol. 23, pp. 7-28, (2011).
European Society of Cardiology, Standards of heart rate variability, vol. 17, Mar. 1996.
Fairchild et al. , perinatology.theclinics.com, "Heart Rate Characteristics: Physiomarkers for Detection of Late-Onset Neonatal Sepsis", vol. 37, pp. 581-598, (2010).
Fairchild et al., The American Physiological Society, "Pathogen-induced heart rate changes associated with cholinergic nervous system activation", (2011).
Fairchild et al., CO-Pediatrics, "Predictive monitoring for early detection of sepsis in neonatal ICU patients", vol. 25, No. 2, Apr. 2013.
Fairchild et al., Pediatric Research, "Septicemia mortality reduction in neonates in a heart rate characteristics monitoring trial", vol. 74, No. 5, Nov. 2013.
Fairchild et al., Am J Perinatol. Author manuscript, "Cross-correlation of heart rate and oxygen saturation in very low birthweight infants: Association with apnea and adverse events", vol. 35, No. 5, pp. 463-469, Apr. 2018.
Fairchild et al., International Pediatric Research Foundation, Inc., "Oxygen desaturations in the early neonatal period predict development of bronchopulmonary dysplasia", Oct. 9, 2018.
Farrow et al., Respiratory Physiology & Neurobiology, "Mitochondrial oxidant stress increases PDE5 activity in persistent pulmonary hypertension of the newborn", vol. 174, pp. 272-281, (2010).
Farrow et al., Antioxidants & Redox Signaling, "Brief Hyperoxia Increases Mitochondrial Oxidationand Increases Phosphodiesterase 5 Activity in Fetal Pulmonary Artery Smooth Muscle Cells", vol. 17, No. 3, (2012).
Fyfe et al., Sleep Medicine Reviews, "The development of cardiovascular and cerebral vascular control in preterm infants", vol. 18, (2014).
Fyfe et al., Sleep, "The Effect of Gestational Age at Birth on Post-Term Maturation of Heart Rate Variability", vol. 38, No. 10, (2015).
Gerschman et al., Science, "Oxygen Poisoning and X-irradiation: A Mechanism in Common", vol. 119, pp. 623-626, May 7, 1954.
Goedicke-Fritz et al., PersPective, "Preterm Birth Affects the risk of Developing immune-Mediated Diseases", Oct. 9, 2017.
Goel et al., The Journal of Pediatrics, "Predicting Extubation Outcomes—A Model Incorporating Heart Rate Characteristics Index", vol. 195, Apr. 2018.
Greenough, Seminars in Fetal & Neonatal Medicine, "Long term respiratory outcomes of very premature birth (<32 weeks)", vol. 17, (2012).
Griffin et al., J Cardiovasc Electrophysiol, " The Dynamic Range of Neonatal Heart Rate Variability", vol. 5, pp. 112-124, Feb. 1994.
Griffin et al., Pediatrics, "Toward the Early Diagnosis of Neonatal Sepsis and Sepsis-Like Illness Using Novel Heart Rate Analysis", vol. 107, pp. 97-104, (2001).
Griffin et al., Pediatric Research, "Abnormal Heart Rate Characteristics Preceding Neonatal Sepsis and Sepsis-Like Illness", vol. 53, No. 6, (2003).
Griffin et al., Pediatric Research, "Abnormal Heart Rate Characteristics Are Associated with Neonatal Mortality", vol. 55, No. 5, (2004).
Griffin et al., Pediatrics, "Heart Rate Characteristics: Novel Physiomarkers to Predict Neonatal Infection and Death", vol. 16, pp. 1070-1074, (2005).
Griffin et al., Pediatrics, "Heart Rate Characteristics and Laboratory Tests in Neonatal Sepsis", vol. 115, pp. 937-941, (2005).
Griffin et al., Pediatric Research, "Heart Rate Characteristics and Clinical Signs in Neonatal Sepsis", vol. 61, pp. 222-227 (2007).
Haddad et al., Contemporary Reviews in Cardiovascular Medicine, "Right Ventricular Function in Cardiovascular Disease, Part IIPathophysiology, Clinical Importance, and Management of Right Ventricular Failure", Apr. 1, 2008.
Higgins et al., The Journal of Pediatrics, "Bronchopulmonary Dysplasia: Executive Summary of a Workshop", vol. 197, Jun. 2018.
Hooper et al., International Pediatric Research Foundation, Inc., "Cardiovascular transition at birth: a physiological sequence", vol. 77, No. 5, May 2015.
Huston et al., The Association for the Publication of the Journal of Internal Medicine, "The pulse of inflammation: heart rate variability, the cholinergic anti-inflammatory pathway and implications for therapy", vol. 269, pp. 45-53, (2010).
Iliodromiti et al., J Matern Fetal Neonatal Med., "Acute lung injury in preterm fetuses and neonates: mechanisms and molecular pathways", vol. 26, No. 17, pp. 1696-1704, May 20, 2013.
Ilizarov et al., Am. J. Respir. Cell Mol. Bio., "Overexpression of Manganese Superoxide Dismutase Protects Lung Epithelial Cells against Oxidant Injury", vol. 24, pp. 436-441, (2001).
Behrman et al., Institute of Medicine, "Preterm Birth: Causes, Consequences, and Prevention", (2007).
Javorka et al., Physiol. Res., "Heart Rate Variability in Newborns" , vol. 66, No. 2, pp. 203-214, Apr. 30, 2017.
Jensen et al., Birth Defects Research (Part A), "Epidemiology of Bronchopulmonary Dysplasia", vol. 100, pp. 145-157, (2014).
Jhaveri Sanghvi et al., Neonatology, "Pulmonary Resilience: Moderating the Association between Oxygen Exposure and Pulmonary Outcomes in Extremely Preterm Newborns", May 12, 2022.
Jobe et al., American Journal of Respiratory and Critical Care Medicine, "Bronchopulmonary Dysplasia", vol. 163, (2001).
Johnson et al., The Journal of Pediatrics, "Cost of Morbidities in Very Low Birth Weight Infants" vol. 162, No. 2, (2013).
Jonston et al., Journal of the Intensive Care Society, "Heart rate variability: Measurement and emerging use in critical care medicine", vol. 21(2), pp. 148-157, (2020).
Joshi et al., Scientific Reports, "Statistical Modeling of Heart Rate Variability to Unravel the Factors Affecting Autonomic Regulation in Preterm Infants", May 22, 2019.
Kaczmarek et al., Neonatology, "Heart Rate Variability and Extubation Readiness in Extremely Preterm Infants", vol. 104, pp. 42-48, May 24, 2013.
Kalikkot Thekkeveedu et al., Respiratory Medicine, "Bronchopulmonary dysplasia: A review of pathogenesis and pathophysiology", vol. 132, pp. 170-177, (2017).

(56) References Cited

OTHER PUBLICATIONS

Karin et al., Nature Immunology, "NF-κB at the crossroads of life and death", Vo. 3 No. 3, Mar. 2002.
Khattak et al., Early Human Development, "Longitudinal assessment of heart rate variability in very low birth weight infants during their NICU stay", Jul. 19, 2006.
Khemani et al., Pediatrics, "Pulmonary Artery Hypertension in Formerly Premature Infants With Bronchopulmonary Dysplasia: Clinical Features and Outcomes in the Surfactant Era", (2007).
Kielt et al., The Journal of Pediatrics, "Non-Invasive Respiratory Severity Indices Predict Adverse Outcomes in Bronchopulmonary Dysplasia", Nov. 5, 2021.
Kovatchev et al., Pediatric Research, "Sample Asymmetry Analysis of Heart Rate Characteristics with Application to Neonatal Sepsis and Systemic Inflammatory Response Syndrome", vol. 54, No. 6, (2003).
Kriebel et al., American Journal of Public Health, "Reenergizing Public Health Through Precaution", vol. 91, No. 9, Sep. 2001.
Kummer, Proc Am Thorac Soc., "Pulmonary Vascular Innervation and Its Role in Responses to Hypoxia", vol. 8, pp. 471-476, (2011).
Kwon et al., Neonatology, "Long-Term Outcomes of Pulmonary Hypertension in Preterm Infants with Bronchopulmonary Dysplasia", vol. 110, pp. 181-189, (2016).
Lake et al., Am J Physiol Regul Integr Comp Physiol, "Sample entropy analysis of neonatal heart rate variability", vol. 283. pp. 789-797, May 26, 2002.
Latremouille et al., Respiratory Care, "Heart Rate Variability in Extremely Preterm Infants Receiving Nasal CPAP and Non-Synchronized Noninvasive Ventilation Immediately After Extubation", vol. 63, No. 1, pp. 62-69, Jan. 2018.
Latremouille et al., Pediatric Pulmonology, "The effects of nasal continuous positive airway pressure and high flow nasal cannula on heart rate variability in extremely preterm infants after extubation: A randomized crossover trial", vol. 54, pp. 788-796, Jan. 22, 2019.
Laughon et al., Pediatrics, "Patterns of Respiratory Disease During the First 2Postnatal Weeks in Extremely Premature Infants", vol. 123, No. 4, Apr. 2009.
Laughon et al., Am J Respir Crit Care Med., "Prediction of Bronchopulmonary Dysplasia by Postnatal Age in Extremely Premature Infants" vol. 183. pp 1715-1722, Mar. 4, 2011.
Thiriez et al., Clin Auton Res, "Altered autonomic control in preterm newborns with impaired neurological outcomes" vol. 25, pp. 233-242, Aug. 8, 2015.
Tracey, Nature, "The inflammatory reflex", vol. 420, Dec. 2002.
Ubags et al., Eur Respir Rev, "Early origins of lung disease: towards an interdisciplinary approach", Aug. 18, 2020.
Sanghvi, Thesis/PHD Dissertation, "Pulmonary Resilience: Moderating the Association Between Oxygen Exposure and Short-Term Respiratory Outcomes in Extremely Preterm Newborns", May 20, 2022.
Vaillancourt et al., Respiratory Research, "Autonomic nervous system involvement in pulmonary arterial hypertension", pp. 1-15, (2017).
Van Marter et al., The Journal of Pediatrics, "Chorioamnionitis, mechanical ventilation, and postnatal sepsis as modulators of chronic lung disease in preterm infants", Feb. 2002.
Van Marter, Seminars in Fetal & Neonatal Medicine, "Epidemiology of bronchopulmonary dysplasia", vol. 14, pp. 358-366, (2009).
Van Zanten et al., Arch Dis Child Fetal Neonatal Ed, "The risk for hyperoxaemia after apnoea, bradycardia and hypoxaemia in preterm infants", Mar. 25, 2014.
Wai et al., The Journal of Pediatrics, "Early Cumulative Supplemental Oxygen Predicts Bronchopulmonary Dysplasia in High Risk Extremely Low Gestational Age Newborns", vol. 177, Oct. 2016.
Wakai, Experimental Neurology, "Assessment of fetal neurodevelopment via fetal magnetocardiography", vol. 190, Jun. 15, 2004.
Wang et al., Gene, "Oxidative stress and bronchopulmonary dysplasia", vol. 678, pp. 177-183, (2018).
Wedgwood, et al., Am J Physiol Lung Cell Mol Physiol, "Increased hydrogen peroxide downregulates soluble guanylate cyclase in the lungs of lambs with persistent pulmonary hypertension of the newborn", vol. 289, pp. 660-666, May 29, 2005.
Westrup et al., Journal of Perinatology, "Family-centered developmental supportive care: a holistic and humane approach to reduce stress and pain in neonates", vol. 27, pp. 12-18 (2007).
Wilborn et al., Pediatric Research, "Oxygen Toxicity to the Developing Lung of the Mouse: Role of Reactive Oxygen Species", vol. 40, pp. 225-232, Aug. 4, 1996.
Wood, Biometrika, "On p. values for smooth components of an extended generalized additive model", vol. 100, pp. 221-228, (2013).
Wright et al., Am J Physiol Lung Cell Mol Physiol, "Hyperoxia-induced NF-IB activation occurs via a maturationally sensitive atypical pathway", vol. 296, Mar. 2009.
Yang et al., Q J Med, "A novel regulator of lung inflammation and immunity: pulmonary parasympathetic inflammatory reflex", vol. 107, pp. 789-792, Jan. 18, 2014.
Yiallourou et al., Ealy Human Development, "The development of autonomic cardiovascular control is altered by preterm birth", vol. 89, pp. 145-152, (2013).
Sanghvi et al., Neonatology, "Pulmonary Resilience: Moderating the Association between Oxygen Exposure and Pulmonary Outcomes in Extremely Preterm Newborns", vol. 119, pp. 433-442, May 12, 2022.
Leon et al., IEEE Journal of Biomedical and Health Informatics, "Early detection of late onset sepsis in premature infants using visibility graph analysis of heart rate variability", pp. 2168-2194, (2020).
Leroy et al., The Journal of Pediatrics, "A Time-Based Analysis of Inflammation in Infants at Risk of Bronchopulmonary Dysplasia", vol. 192, Jan. 2018.
Lignelli et al., Am J Physiol Lung Cell Mol Physiol, "Recent advances in our understanding of the mechanisms of lung alveolarization and bronchopulmonary dysplasia", vol. 317, pp. 832-887, Oct. 7, 2019.
Longin et al., J. Perinat. Med. "Maturation of the autonomic nervous system: differences in heart rate variability in premature vs. term infants", vol. 34, pp. 303-308, (2006).
Lucchini et al., Medical & Biological Engineering & Computing, "Multi-parametric cardiorespiratory analysis in late-preterm, early-term, and full-term infants at birth", vol. 57, pp. 99-106, (2019).
Marseglia et al., Free Radical Biology and Medicine, "Role of oxidative stress in neonatal respiratory distress syndrome", Apr. 23, 2019.
Martin et al., Clin Perinatol, "Hypoxic Episodes in Bronchopulmonary Dysplasia", vol. 42, pp. 825-838, (2015).
Martin et al., National Vital Statistics Reports, "Births: Final Data for 2019", vol. 70, No. 2, Mar. 23, 2021.
Mccarley et al., Neonatal Network, "Implementing a Systematic Process for Consistent Nursing Care in a NICU: A Quality Improvement Project", vol. 37, No. 2, Mar./Apr. 2018.
Medford, Nursing Science Quarterly, "A Theory of Health Promotion for Preterm Infants Based on Levine's Conservation Model of Nursing", vol. 17, No. 3, Jul. 2004.
Medford et al., Journal of Nursing Management, "Evaluating nurse staffing patterns and neonatal intensive care unit outcomes using Levine's conservation model of nursing", vol. 19, pp. 998-1011, Sep. 2011.
Mignini et al., Autonomic & Autacoid Pharmacology, "Autonomic innervation of immune organs and neuroimmune modulation", vol. 23, pp. 1-25, (2003).
Monroe et al., Psychological Bulletin, "Diathesis-Stress Theories in the Context of Life Stress Research: Implications for the Depressive Disorders", vol. 110, No. 3, pp. 406-425 (1991).
Mooreman et al., IEEE Transactions on Biomedical Engineering, "Heart Rate Characteristics Monitoring for Neonatal Sepsis", vol. 53, No. 1, Jan. 2006.
Mooreman et al., The Journal of Pediatrics, "Mortality Reduction by Heart Rate Characteristic Monitoring in Very Low Birth Weight Neonates: A Randomized Trial", vol. 159, No. 6, Dec. 2011.
Moreira et al., American Journal of Pediatrics, "Heart Rate Characteristic Index Monitoring for Early Detection of Infections in Very Low Birth Weight Infants", vol. 5, No. 3, pp. 170-174, Aug. 28, 2019.

(56) References Cited

OTHER PUBLICATIONS

Morty, Seminars in Perinatology, "Recent advances in the pathogenesis of BPD", (2018).
Mourani et al., Am J Respir Crit Care Med, "Pulmonary Vascular Effects of Inhaled Nitric Oxide and Oxygen Tension in Bronchopulmonary Dysplasia", vol. 170, pp. 1006-1013, Jun. 4, 2004.
Mrowka et al., IEEE Engineering in Medicine and Biology, "The Complexity of Heart Rate in Its Postnatal Development; The Role of Sleep Stages and Age in the Development of Heart Rate Control Complexity ", Mar./Apr. 2001.
Mulkey et al., Early Human Development, "Autonomic nervous system depression at term in neurologically normal premature infants", vol. 123, pp. 11-16, Jul. 11, 2018.
Mulkey et al., Pediatric Research, "Autonomic nervous system maturation in the premature extrauterine milieu", Apr. 28, 2020.
Nakamura et al., BioSystems, "Identification of development and autonomic nerve activity from heart rate variability in preterm infants", vol. 79, pp. 117-124, (2005).
Nelson et al., Pediatric Research, "Probing the Order within Neonatal Heart Rate Variability", vol. 43, pp. 823-831, (1998).
Oliveira et al., Frontiers in Physiology, "Early Postnatal Heart Rate Variability in Healthy Newborn Infants", vol. 10, Article 922, Aug. 7, 2019.
Patural et al., Clin Auton Res, "Birth prematurity determines prolonged autonomic nervous system immaturity", vol. 14, pp. 391-395, Jun. 24, 2004.
Patural et al., Early Human Development, "Autonomic cardiac control of very preterm newborns: A prolonged dysfunction", vol. 84, pp. 681-687, Apr. 30, 2008.
Pavlov, Bioelectronic Medicine, Collateral benefits of studying the vagus nerve in bioelectronic medicine, (2019).
Perez et al., Free Radical Biology and Medicine, "Oxygen radical disease in the newborn, revisited: Oxidative stress and disease in the newborn period", vol. 42, pp. 61-72, Apr. 5, 2019.
Pincus, Proc. Natl. Academy of Science USA, "Approximate entropy as a measure of system complexity", vol. 88, pp. 2297-2301, Mar. 1991.
Poets et al., American Medical Association, "Association Between Intermittent Hypoxemia or Bradycardia and Late Death or Disability in Extremely Preterm Infants", vol. 314, No. 6, pp. 595-603, Aug. 11, 2015.
Richman et al., American Journal Physiol Heart Circ Physiol, "Physiological time-series analysis using approximate entropy and sample entropy", vol. 278, pp. 2039-2049, (2000).
Roisman et al., Development and Psychopathology, "Distinguishing differential susceptibility from diathesis-stress: Recommendations for evaluating interaction effects", vol. 24, pp. 389-409, (2012).
Salgado, The European Journal of Psychology Applied to Legal Context, "Transforming the Area under the Normal Curve (AUC) into Cohen's d, Pearson's rpb, Odds-Ratio, and Natural Log Odds-Ratio: Two Conversion Tables", vol. 10, pp. 35-47, Oct. 18, 2017.
Saugstad, Pediatric Research, "Hypoxanthine as an Indicator of Hypoxia: Its Role in Health and Disease through Free Radical Production", vol. 23, No. 2, Oct. 6, 1987.
Saugstad, Journal Perinatal, "Oxygen and oxidative stress in bronchopulmonary dysplasia", vol. 38, pp. 571-577 (2010).
Saugstad et al., Pediatric Research, "Oxygen therapy of the newborn from molecular understanding to clinical practice", vol. 85, pp. 20-29, (2019).
Schlatterer et al., Pediatric Research, "Autonomic development in preterm infants is associated with morbidity of prematurity", Mar. 2, 2021.
Siffel et al., The Journal of Maternal-Fetal & Neonatal Medicine, "Global incidence of bronchopulmonary dysplasia among extremely preterm infants: a systematic literature review", vol. 34, No. 11, pp. 1721-1731, (2021).
Silva et al., Am J Physiol Lung Cell Mol Physiol, "Recent advances in the mechanisms of lung alveolarization and the pathogenesis of bronchopulmonary dysplasia", Sep. 9, 2015.
Silva et al., Journal Perinatal, "Does heart rate variability improve prediction of failed extubation in preterm infants?", vol. 47, No. 2, pp. 252-257, (2019).
Smith et al., Biology of the Neonate, "Characteristics of Heart Perios Variability in Intubated Very Low Birth Weight Infants with Respiratory Disease", vol. 86, No. 4, p. 269-274, Aug. 3, 2004.
Srinivasan et al., Co-Pediatrics, "New technologies for the rapid diagnosis of neonatal sepsis", vol. 24, No. 2, pp. 165-171, Apr. 2012.
Stephan-Blanchard et al., PLOS One, "Heart Rate Variability in Sleeping Preterm Neonates Exposed to Cool and Warm Thermal Conditions", vol. 8, Issue 7, Jul. 1, 2013.
Stevens et al., Pediatric Pulmonology, "Effect of Cumulative Oxygen Exposure on Respiratory Symptoms During Infancy Among VLBW Infants Without Bronchopulmonary Dysplasia", vol. 45, pp. 371-379 (2010).
Stoll et al., JAMA, "Trends in Care Practices, Morbidity, and Mortality of Extremely Preterm Neonates, 1993-2012", vol. 314, No. 10, Sep. 8, 2015.
The Stop-Rop Multicenter Study Group, Pediatrics, "Supplemental Therapeutic Oxygen for Prethreshold Retinopathy of Prematurity (STOP-ROP), A Randomized, Controlled Trial. I: Primary Outcomes", vol. 105, No. 2, Feb. 2000.
Sullivan et al., The Journal of Pediatrics, "Infection and Other Clinical Correlates of Abnormal Heart Rate Characteristics in Preterm Infants", vol. 164, No. 4, (2014).
Sullivan et al., The Journal of Pediatrics, "Early Heart Rate Characteristics Predict Death and Morbidities in Preterm Infants", vol. 174, pp. 57-62, Jul. 2016.
Sweet et al., Neonatology, "European Consensus Guidelines on the Management of Respiratory Distress Syndrome—2019 Update", vol. 115, pp. 432-450, Apr. 11, 2019.
Thebaud et al., Nature Reviews/Disease Primers, "Bronchopulmonary dysplasia", pp. 1-23, Nov. 14, 2019.
European Patent Office, International Search Report and Written Opinion for International Patent Application No. PCT/US2023/024530, Aug. 31, 2023.
Sanoj K M et al. "Oxygen therapy in preterm infants: recommendations for practice", Paediatrics and Child Health, Elsevier, Amsterdam, NL, vol. 31, No. 1 pp. 1-6, Jan. 2021.
Canada Patent Office, Examination Report, Canadian Patent Application No. 3,259,021, Dec. 12, 2025.
Korea Patent Office, Office Action, Korean Patent Application No. 10-2025-7001151, Jan. 28, 2026.
Australia Patent Office, Examination Report, Australian Patent Application No. 2023295185, Jan. 8, 2026.
Japan Patent Office, Office Action, Japanese Patent Application No. 2024-573431, Dec. 5, 2025.
European Patent Office, Office Action, European Patent Application No. 23736519.2, Apr. 22, 2026.

* cited by examiner

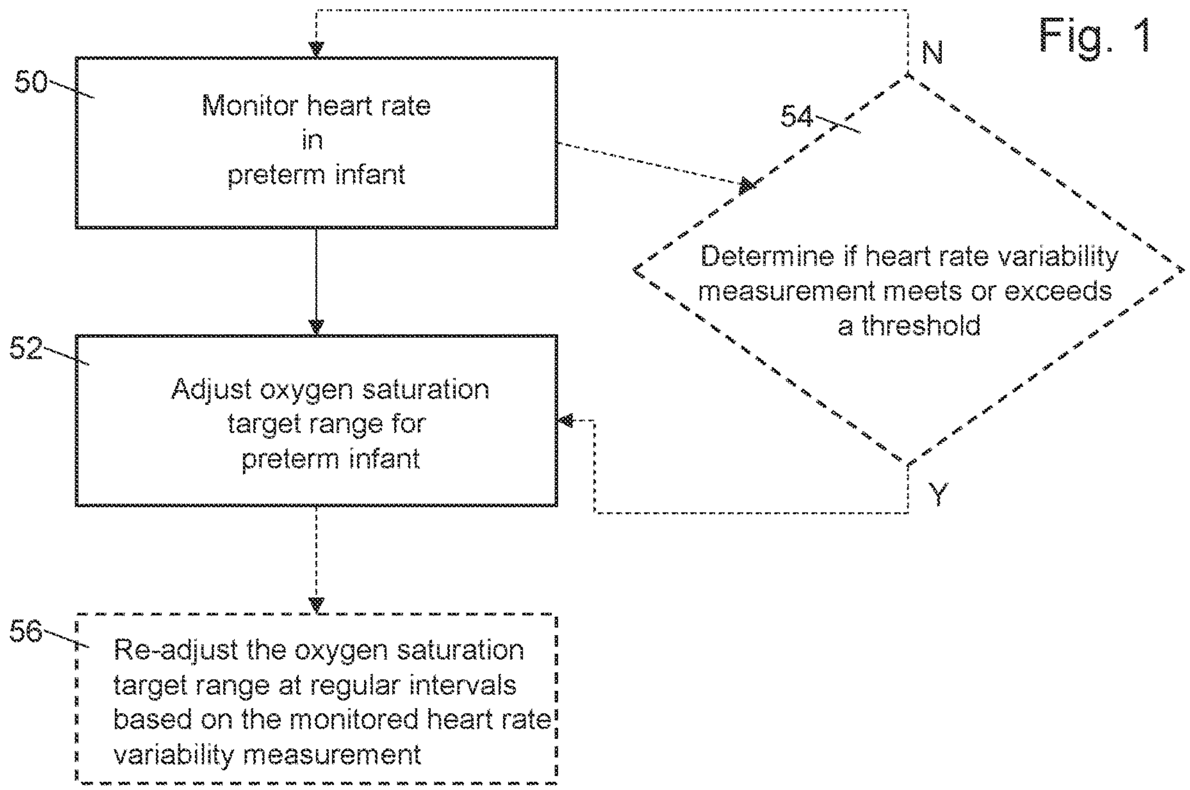
Fig. 1
50
Monitor heart rate in preterm infant
52
Adjust oxygen saturation target range for preterm infant
54
Determine if heart rate variability measurement meets or exceeds a threshold
N
Y
56
Re-adjust the oxygen saturation target range at regular intervals based on the monitored heart rate variability measurement

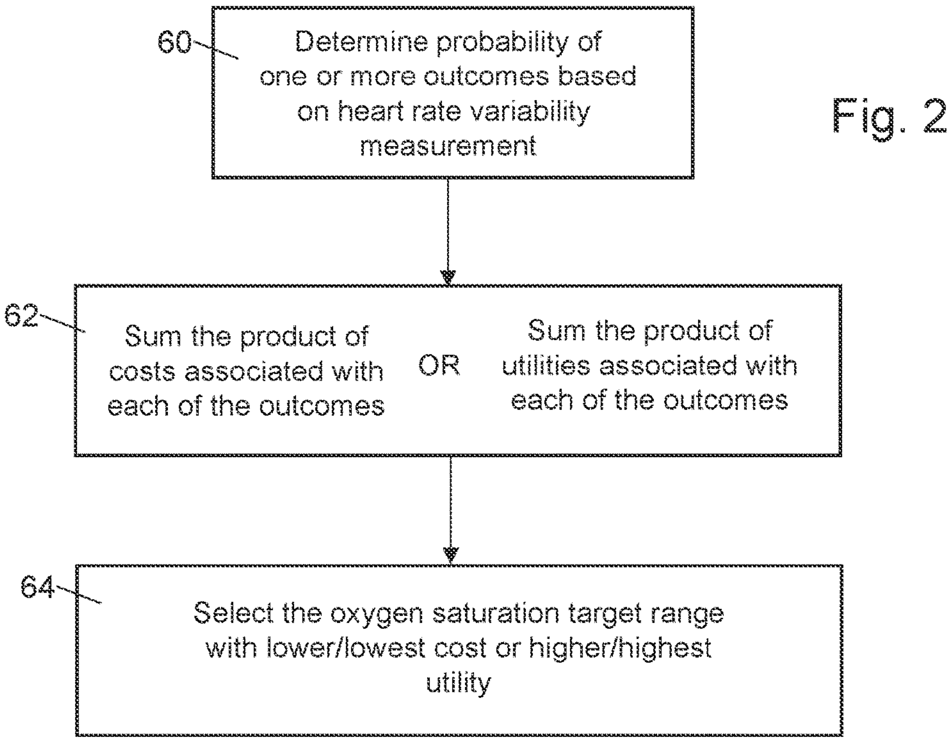
Fig. 2
60
Determine probability of one or more outcomes based on heart rate variability measurement
62
Sum the product of costs associated with each of the outcomes
OR
Sum the product of utilities associated with each of the outcomes
64
Select the oxygen saturation target range with lower/lowest cost or higher/highest utility

METHOD, SYSTEM AND DEVICE FOR INDIVIDUALIZED SUPPLEMENTAL OXYGEN THERAPY FOR PRETERM INFANTS

CROSS-REFERENCE TO RELATED APPLICATIONS

The present application claims the priority benefit of U.S. provisional patent application No. 63/351,706 filed on Jun. 13, 2022, the contents of which are hereby incorporated by reference herein in their entirety.

TECHNICAL FIELD

The present disclosure relates to individualized healthcare, and more particularly to a method, system and device for individualized control of one or more factors affecting health outcomes for preterm infants.

BACKGROUND AND SUMMARY

Bronchopulmonary dysplasia (BPD) is a chronic lung disease of infancy associated with high morbidity and mortality. Extremely preterm newborns encounter a paradox at birth: oxygen is a life-sustaining component of ex uero life yet is undeniably toxic, especially to the preterm infant whose lungs and other organs would otherwise be developing in the low oxygen intrauterine environment. Attempts at minimizing supplemental oxygen exposure by targeting lower oxygen saturations appear to decrease BPD but may increase mortality. Given the potential association between lower oxygen saturations and increased mortality, practice guidelines favor targeting higher saturations. This uniformly increases oxygen exposure, prompting a cascade of pathogenic mechanisms implicated in BPD development.

With these higher target saturations as standard of care, 22-45% of very low birthweight infants are affected by BPD. The downstream implications of BPD are severe: the costs of the initial hospitalization are 2× higher; there is increased risk of late onset sepsis, cerebral palsy, neurodevelopmental impairment, pulmonary morbidity, and double the risk of hospital readmission within the first year; and lifetime socioeconomic impacts on the patient that extend to the family.

While BPD pathogenesis is multifactorial, it is accepted that oxidative stress (OS) contributes to pulmonary inflammation and vascular dysplasia characteristic of its clinical presentation. OS in the preterm newborn is a driver of morbidity and mortality, and which can be referred to as “oxygen radical disease in the newborn”. There is evidence characterizing OS in the preterm lung and highlighting mechanisms by which it influences pulmonary inflammation and vascular changes. Reactive oxygen species (ROS) include molecules that are free radicals which are highly toxic to cells. OS can occur in term infants but preterm newborns are at greater risk because of: (1) increased free iron available for additional free radical creation; (2) the environmental challenge of preterm birth with transition to air from the low-oxygen uterus; (3) the likelihood of needing supplemental oxygen for respiratory distress and insufficiency; and (4) an impaired antioxidant defense system. Multiple organs in the preterm infant are susceptible to OS-induced injury, and oxygen radical disease in the newborn can lead to manifestation of diseases consequent to preterm birth, such as BPD, necrotizing enterocolitis (NEC), and retinopathy of prematurity (ROP; which itself leads to increased risk of blindness).

The Neonatal Oxygenation Prospective Meta-analysis (NeOProM) found that in infants less than twenty-eight weeks gestational age (GA), targeting an oxygen saturation ($SpO_2$) range of 85-89% vs. 91-95% resulted in lower rates of ROP but increased the risk of death. Currently, physiologic parameters to optimize oxygen delivery to reduce morbidity and mortality are limited. For example, attempts at minimizing supplemental oxygen exposure can decrease morbidity but increase mortality. The amount of supplemental oxygen therapy administered is determined by targeting an oxygen saturation range measured by pulse oximetry, often by setting alarm limits on the pulse oximeter, but the optimal target that achieves a balance between optimal benefit and minimizing harm remains unknown. There is thus a clinical challenge in that efforts to minimize oxygen exposure and decrease the incidence of oxygen radical diseases can be outweighed by concerns of increased mortality. To date, standard recommendations prescribe uniform saturation targets favoring the higher oxygen exposure for all preterm newborns in the neonatal intensive care unit (NICU) to minimize mortality, even though this may be over-oxygenating some or most infants.

In various embodiments, the present disclosure addresses the above challenges and more through, among other things, measuring pulmonary resilience and autonomic nervous system (ANS) activity through heart rate signal analysis. Pulmonary resilience is a homeostatic process driven by the ANS as a moderator of physiologic stress that when functional, can inform successful environmental adaptation following extremely preterm birth. Early life ANS function can explain individual differences in the association between cumulative supplemental oxygen (CSO) exposure and short-term respiratory outcomes. A pulmonary resilience measurement (PRM) can include, among other things, one or more of heart rate (HR), mean, median and standard deviation of heart rate, measures of heart rate decelerations and accelerations, heart rate variability (HRV), Heart Rate Characteristics (HRC), the HRC index (HRCi), heart rate entropy, vagal tone, and parasympathetic/sympathetic balance. PRMs modify the association between early life oxygen exposure and short-term respiratory outcomes.

The ANS operates at the subconscious level and serves to make routine adjustments to various physiological systems, responding to needs related to body temperature, and coordination of cardiovascular, respiratory, digestive, excretory, and reproductive functions. The sympathetic and parasympathetic branches of the ANS develop independently during fetal life. The sympathetic branch, responsible for the fight-or-flight response and increased HR, develops rapidly in the first trimester and at a slower rate thereafter; the parasympathetic branch, responsible for the rest-and-digest response and decreased HR, develops considerably at twenty-five to thirty weeks gestational age (GA). An immature and underdeveloped ANS can lead to irregularities and rapid fluctuations in HR, and HRV is influenced by sleep states and postnatal growth and development.

Electrical and neurological activity patterns of preterm newborns have been characterized by predominance of an active sleep state, and measures of HRV indicate an increase in sympathetic activity, a decrease in parasympathetic activity and a decrease in overall ANS complexity and adaptability. Postnatal ANS development and maturation, through the study of HRV, is correlated with increasing GA and postnatal age. Analysis of HRV features have indicated that both sympathetic and parasympathetic tone were lowest among infants born most preterm and lower compared to term infants. Furthermore, the early life of the preterm newborn is characterized by sympathetic nervous system activity dominance and decreased parasympathetic nervous system activity, and this imbalance is further altered by postnatal complications and morbidity. When compared with healthy controls, HRV was more compromised in intrauterine growth restricted (IUGR) preterm newborns and in preterm newborns exposed to smoking in utero, both risk factors for BPD and other complications of prematurity. Thus, ANS functional immaturity, and possibly dysregulated interaction between its two branches, is an anticipated consequence of preterm birth. The degree of this dysfunction and how it influences regulation of the inflammatory neural reflex may have consequences for both short- and long-term outcomes in the preterm infant but remains understudied.

The clinical relevance of ANS dysfunction has been described in critically ill adult patients, and implicated in disorders such as multi-organ failure, sepsis, myocardial infarction, decompensated heart failure, and severe brain injury. The ANS maintains homeostasis by making routine adjustments to various physiological systems. The sympathetic and parasympathetic nerves of the ANS relay peripheral events from all systems, including from the vascular bed of the lungs and components of the immune system, to the regulatory centers in the brainstem responsible for cardiorespiratory changes. As heart rate and rhythm are continuously adjusted by the ANS in response to the body's needs, HRV is a non-invasive measure of ANS function defined as the change in the length of time between successive heart beats. ANS function, as measured by HRV, has been studied and characterized in fetal and neonatal development, and a well-known clinical use of HRV is the monitoring of fetal HRV to detect fetal distress. Detecting unique signatures of variability in fetal heart rate, such as transient decelerations, may signify a fetus in distress, and this monitoring has led to significant reductions in morbidity and mortality.

The level of early life ANS activity, an indicator of pulmonary resilience, can moderate the association between oxygen exposure and respiratory outcomes that may be consequential for overall outcomes such as mortality and BPD, NEC, and ROP. In embodiments of the present disclosure, ANS function is measured to inform clinicians as to optimal supplemental oxygen dosing facilitating environmental adaption after preterm birth while minimizing toxicity from overdosing that may be occurring with the current strategy of uniformly targeting higher saturation ranges.

HRC are a specific subset of HRV that have been selected or developed to identify abnormalities in preterm infants' HR patterns. Previous studies have demonstrated that the HRCi (a.k.a. HeRO Score) predicts various neonatal morbidities, including sepsis, urinary tract infection, NEC, meningitis, respiratory decompensation, extubation readiness, and death; and is associated with cytokines. According to the present disclosure, aspects of HRCi and/or some of the intermediate calculations associated with HRCi can be employed to dynamically adjust oxygen saturation target range for preterm infants. For example, patients with low HRCi are or may be at low risk of death and can be potentially safely oxygenated at 85-89%. As the HRCi rises, the risk of death increases, and these infants should be managed at a higher oxygen saturation target range. Furthermore, aspects of HRCi and/or some of the intermediate calculations associated with HRCi can be employed along with other factors to measure pulmonary resilience. And this PRM can be employed to dynamically adjust oxygen saturation target range for preterm infants. Thus, only the patients that are at risk of mortality are placed at risk of BPD or ROP.

In various embodiments, a method, system and/or device according to the present disclosure facilitates individualized control of one or more factors such as targeted oxygen saturation range for preterm infants. In exemplary embodiments, oxygen saturation for preterm infants is dynamically targeted by monitoring the heart rate to determine a HRV measurement and/or measuring the PRM in a preterm infant and adjusting an oxygen saturation target range for the preterm infant. It will be appreciated that adjusting the oxygen saturation target range is or can be based on the HRV measurement and/or PRM. In various embodiments, the HRV measurement and/or PRM is evaluated against a pre-established threshold, and if the HRV measurement and/or PRM meets or exceeds the pre-established threshold, the oxygen saturation target range is adjusted. Embodiments of the present disclosure can further optionally re-adjust the oxygen saturation target range at regular time intervals based on the HRV measurement and/or PRM.

In various embodiments, one or more thresholds can be established for monitored conditions. When a measurement threshold is matched or exceeded, an alert can be generated. The alert can provide a recommended course of action, for example. In various embodiments, the alert can provide instructions to an autonomous device or a human-monitored electronic device to take instructed action. For example, upon a HRV measurement meeting or exceeding a threshold, an alert can be issued to an oxygenation device (such as a standard ventilator, a high-frequency oscillatory ventilator, continuous positive air pressure device, nasal cannula, or other device for supplementing oxygen delivery) or a human-monitored electronic device to adjust oxygen to a patient based on a determined oxygen saturation target range.

An exemplary system according to the present disclosure employs a monitoring device and a device adapted to receive alerts based on operations according to the present disclosure that are triggered according to measurements received from the monitoring device as disclosed herein.

Embodiments of the present disclosure assist in dynamically optimizing preterm infants' oxygen saturation target range in a manner that is individualized to the infants' physiological state.

BRIEF DESCRIPTION OF THE DRAWINGS

FIGS. 1 and 2 are flow diagrams illustrating exemplary methods in accordance with embodiments of the present disclosure.

DETAILED DESCRIPTION OF EMBODIMENTS

Figure 3:
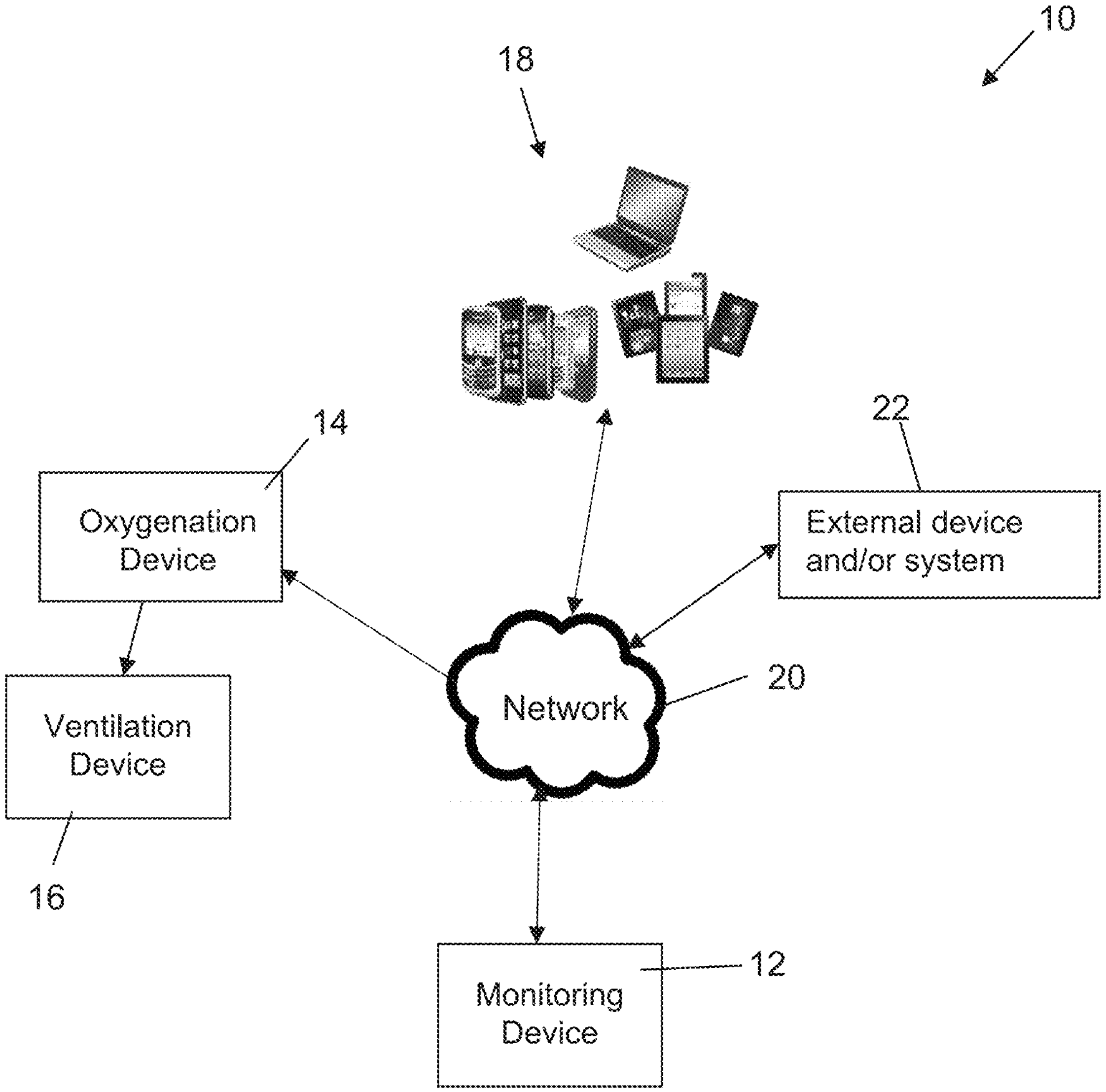
FIG. 3 is a schematic diagram of an exemplary system in accordance with embodiments of the present disclosure.

The foregoing and other aspects of the present disclosure will now be described in more detail with respect to the description and methodologies provided herein. It should be appreciated that the disclosure can be embodied in different forms and should not be construed as limited to the embodiments set forth herein. Rather, these embodiments are provided so that this disclosure will be thorough and complete, and will fully convey the scope of the disclosure to those skilled in the art.

The terminology used in the description of the disclosure herein is for the purpose of describing particular embodiments only and is not intended to be limiting of the disclosure. As used in the description of the embodiments of the disclosure and the appended claims, the singular forms "a", "an" and "the" are intended to include the plural forms as well, unless the context clearly indicates otherwise. For example, a measurement can include one or more measurements, a processor can include one or more processors, and so forth. Also, as used herein, "and/or" refers to and encompasses any and all possible combinations of one or more of the associated listed items.

As used herein, the terms "comprise," "comprises," "comprising," "include," "includes" and "including" specify the presence of stated features, integers, steps, operations, elements, and/or components, but do not preclude the presence or addition of one or more other features, integers, steps, operations, elements, components, and/or groups thereof.

In various embodiments, a method according to the present disclosure dynamically targets oxygen saturation for preterm infants. As shown in FIG. 1, the method includes, as at 50, monitoring, via a monitoring device, the heart rate in a preterm infant to determine a HRV measurement and, as at 52, adjusting an oxygen saturation target range for the preterm infant. It will be appreciated that adjusting the oxygen saturation target range is or can be based on the HRV measurement. In various embodiments, the method can optionally determine if the HRV measurement meets or exceeds a pre-established threshold, as at 54 and indicated in dashed lines. If the HRV measurement does not meet or exceed a pre-established threshold, the method returns to 50. If the HRV measurement meets or exceed a pre-established threshold, the method proceeds to 52. In various embodiments, the method can further optionally re-adjust the oxygen saturation range at regular time intervals based on the HRV measurement, as indicated in dashed lines at 56.

As an example, a pre-established threshold of an HRCi score of 2.0 may be established, and if the measured HRV generates an HRCi score that is above this threshold, no change is made to an established default oxygen saturation target range (e.g., the range may be held at 91-95%). Alternatively, if the measured HRV generates an HRCi score that is below this threshold, the oxygen saturation target range is adjusted to a new range (e.g., 85-89%). As another example, the method of the present disclosure adds the HRCi score as determined by the measured HRV to a baseline or default oxygen saturation target range. In various embodiments, this range adjustment is made along a continuum starting from a low default range. For example, if the default range is 85-89%, and the HRCi score is below 1, the oxygen saturation target range would remain at 85-89%, but if the HRCi score is 1, the oxygen saturation target range is adjusted upward by 1% at the low and high end points to 86-90%, if the HRCi score is 2, the oxygen saturation target range is adjusted upward by 2% at the low and high end points to 87-91%, etc. It will be appreciated that an HRCi score can be determined based on the measured HRV in accordance with methods as described, for example, in U.S. Pat. No. 6,216,032 to Griffin et al., the disclosure of which is incorporated by reference herein in its entirety.

With reference to FIG. 2, a pre-established threshold can be determined by, as at 60, determining the probabilities of one or more outcomes based on the HRV measurement. In various embodiments, this can be determined at both a low and a high oxygen saturation target range. In other embodiments, this can be determined at a continuum of oxygen saturation target ranges. As at 62, embodiments of the method can add the product of costs or utilities associated with each of the one or more outcomes, where each cost or utility is weighted by a predicted probability. As at 64, embodiments of the method then select the oxygen saturation target range that has the lower or lowest cost, or a higher or highest utility.

For example, embodiments of the present disclosure use measurements of HRV to provide dynamic, individualized probabilities of patient outcomes, such as death.

Using the framework of a Bayesian Classifier, for example, a binary decision can be made to select either high or low oxygen saturation target range for a particular patient at a particular time. For that patient at that time, a recent measurement of HRV can be used to estimate the patient's dynamic probability of outcomes including mortality and various morbidities. One can further estimate the patient's probability of a number of outcomes if the patient were in either the low or high oxygen saturation target range group. The patient's probability of each outcome can be multiplied by the cost associated with the outcome, and the quantities can be summed separately for low and high oxygen saturation target range groups. Finally, the oxygen saturation target range can be selected that minimizes the total costs associated with the predicted outcomes. For example, the US Department of Health and Human Services (HHS) published lifetime costs in 2003 USD associated with intellectual impairment, cerebral palsy, hearing loss, and vision impairment as $1,014,000, $921,000, $417,000, and $566,000, respectively. HHS published the value of a statistical life in 2014 USD as $9.3M (or $7.2M in 2003 USD). If one estimated the probabilities of death, intellectual impairment, cerebral palsy, hearing loss, and vision impairment for a particular patient at a particular time as 20%, 20%, 10%, 5%, and 5%, respectively, if the patient were in the low oxygen saturation target range, and 15%, 25%, 15%, 10%, and 10%, respectively, in the high oxygen saturation target range, then the expected cost of choosing the low oxygen saturation target range is $1,784,050 (20%×$7.2M+20%×$1,014,000+10%×$921,000+5%×$417,000+5%×$566,000) versus $1,569,950 in the high oxygen saturation target range (15%×$7.2M+25%×$1,014,000+15%×$921,000+10%×$417,000+10%×$566,000), and one would choose the high oxygen saturation target range. In various embodiments, the patient's probability of the outcome can be multiplied by a benefit or utility associated with the outcome, and the quantities can be summed separately for low and high oxygen saturation target range groups. In such cases, the oxygen saturation target range can be selected that maximizes the total utilities or benefits associated with the predicted outcomes. One common example of a benefit associated with certain healthcare related outcomes is a Quality Adjusted Life Year (QALY), and the calculations would be similar to those above for costs and would finish with selecting the oxygen saturation target range that maximizes expected QALYs.

In various embodiments, a linear interpolation can be used to estimate the probability of some or all of the morbidities associated with oxygen saturation target ranges that lie on a continuum. Similarly, a weighted cost can be calculated for each range within the continuum by summing the product of the costs and/or utilities along with the respective probabilities. Finally, the oxygen saturation target range can be selected to minimize the total costs and/or maximize the total utilities. Extending the binary cost example from above, one might estimate that a middle oxygen saturation target range of 88-92% has a probability of death of 16% based on HRV, and the other outcomes estimated using linear interpolation as 22.5%, 12.5%, 7.5%, and 7.5% for intellectual impairment, cerebral palsy, blindness, and deafness, respectively. This would lead one to choose the middle oxygen saturation target range, since it minimizes expected costs, at $1,569,000 (16%×$7.2M+22.5%×$1,014,000+12.5%×$921,000+7.5%×$417,000+7.5%×$566,000).

In various embodiments, one or more thresholds can be established for monitored conditions. When a measurement threshold is matched or exceeded, an alert can be generated. In various embodiments, an alert is a detected event communication based on an event being detected. In various cases, the "event" takes the form of a threshold having been met or exceeded. The alert can provide a recommended course of action, for example. In various embodiments, the alert can provide instructions to an autonomous device to take instructed action. For example, upon a HRV measurement meeting or exceeding a threshold, an alert can be issued regarding the adjusted oxygen saturation range.

As a specific example, with reference to system 10 in FIG. 3, a monitoring device 12 for a preterm infant (i.e., patient) monitors heart rate characteristics such as the HRV in the preterm infant. The monitoring device can include ECG leads, a pulse oximetry sensor, a chest strap, watch, armband or other suitable device or means for monitoring HRV. If the HRV measurement meets or exceeds a pre-established threshold, an alert can be issued to a servo-controlled oxygenation device 14 operable to adjust oxygen flow to keep the preterm infant within an oxygen saturation range. As another example, an alert can be issued to a device 18 employed by a human attendant with instructions for a recommended oxygen saturation range setting or adjustment on the ventilation device 16 for a preterm infant being monitored. Upon receipt, the human attendant can then physically or electronically interact with a pulse oximeter or an oxygenation device 14 to adjust one or more settings on the respective device based on the received recommended oxygen saturation range. It will be appreciated that threshold measurements and determinations as described herein can be performed by a suitable computing device including a processor and a memory storing instructions operable to perform functions as described herein. For example, the monitoring device 12 may have an internal processor and programming to establish thresholds, conduct determinations and issue one or more alerts based on the determinations in accordance with the present disclosure. Such alerts can be communicated via a network 20 to other systems and/or devices in communication with the network 20. In other examples, the monitoring device 12 may communicate raw measurements over the network 20 to an external computing system or device 22, wherein the external computing system or device 22 employs a processor and programming to establish thresholds, conduct determinations and issue one or more alerts based on the determinations in accordance with the present disclosure. For example, the device 22 may be an electronic health record or electronic medical record system, which may be programmed to generate an order that should be sent by a physician to a nurse to modify the target range. In still other examples, the monitoring device 12 may communicate raw measurements over the network 20 to a personal computing device 18, wherein the personal computing device 18 employs a processor and programming to establish thresholds, conduct determinations and issue one or more alerts based on the determinations in accordance with the present disclosure. In various other embodiments, the oxygenation device 14 employs a processor and programming to establish thresholds, conduct determinations, issue alerts and mechanically or electronically operate and adjust supplemental oxygen and/or oxygen saturation range on ventilation device 16 in accordance with the present disclosure.

In various embodiments, the oxygenation device 14 and/or ventilation device 16 can provide a bedside display of real-time PRM to inform dynamic prescribing of oxygenation saturation targets during the administration of supplemental oxygen in accordance with the present disclosure. It will be appreciated that the exact manner of obtaining vital signs and measuring the pulmonary resilience and the subsequent analysis can be accomplished by a multitude of techniques. For example, it may be achieved by taking vital signs and the vital signs samples are analyzed locally, or the information is transferred over a data communications network such as network 20 to another location or computing device (e.g., 14, 18, 22) where subsequent analysis or other processing may take place. Furthermore, data and results may be displayed at any point during the process, in a variety of ways. For example, readings and data may be conveyed to the user by visual media or audible signals (such as voice or tones, for example), or a combination thereof.

It will be appreciated that the network 20 can be a local area network (LAN), a wide area network (WAN), a public network such as the Internet, or a private network. The devices 12, 14, 18 and/or system/device 22 are configured to connect to the network 20 or remote communications link in any suitable manner. In various embodiments, such a connection is accomplished via: a conventional phone line or other data transmission line, a digital subscriber line (DSL), a T-1 line, a coaxial cable, a fiber optic cable, a wireless or wired routing device, a mobile communications network connection (such as a cellular network or mobile Internet network), or any other suitable medium. In various embodiments, system/device 22 is an online-accessible cloud portal or server.

Embodiments of the system 10 can thus include monitoring device 12, which is adapted to monitor the heart rate in a preterm infant to determine a HRV measurement and a computing device such as 14, 18 or 22 adapted to determine a PRM in the preterm infant based on the HRV measurement, determine if the PRM meets or exceeds a pre-established threshold and issue an alert conveying an oxygen saturation target range for the preterm infant, for example. The target range can be adjusted by manually or electronically setting limits on a pulse oximeter device as described elsewhere herein.

Figure 4:
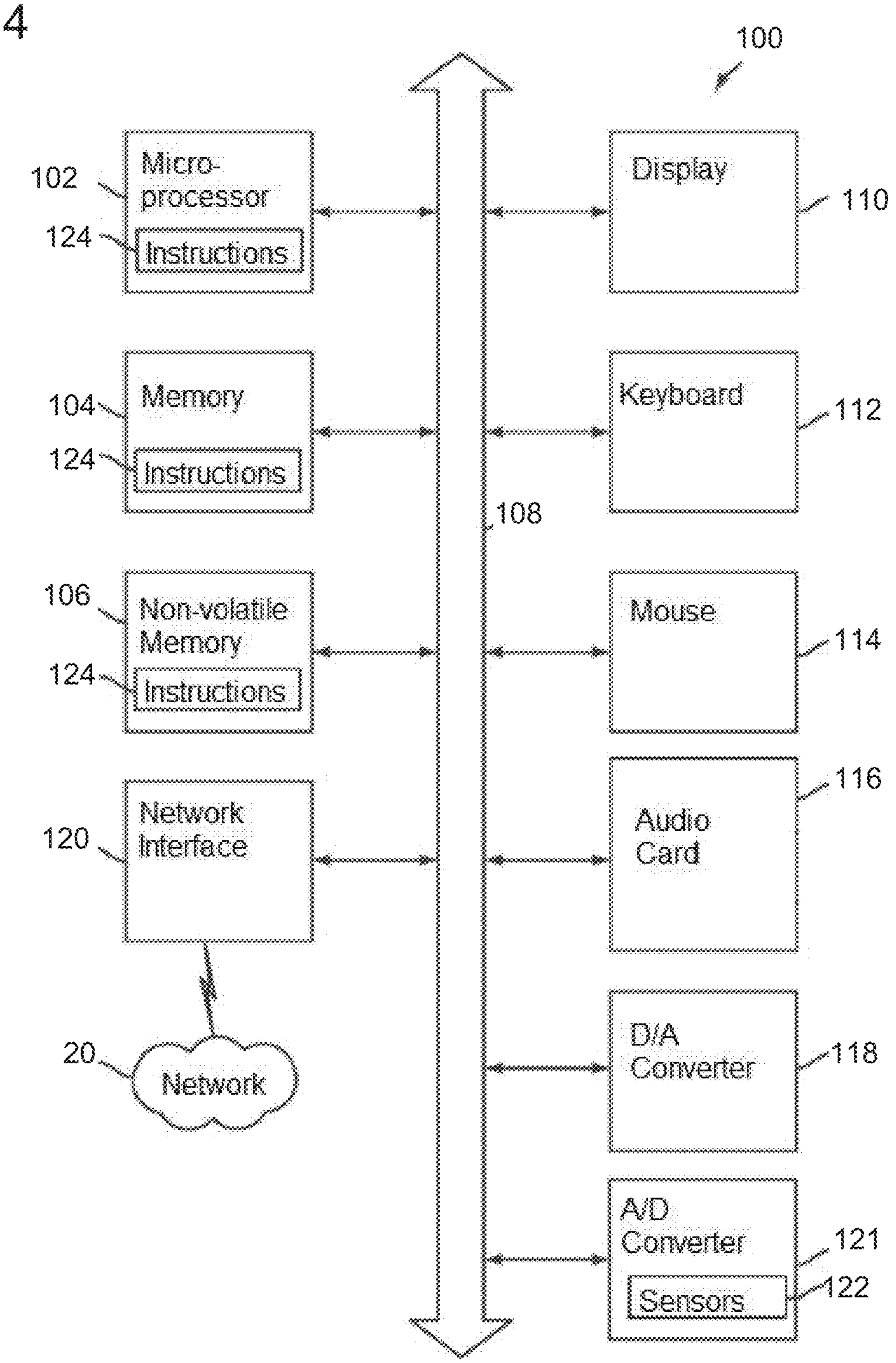
FIG. 4 is a schematic diagram of an exemplary device or machine upon which one or more aspects of embodiments of the present disclosure can be implemented or run.

FIG. 4 is a block diagram illustrating an example of a machine or device 100 upon which one or more aspects of embodiments of the present disclosure can be implemented (or, run). Device 100 is one example; others can include logic, machines with one or more components, circuits, modules, or mechanisms. In an example, one or more computer systems or one or more hardware processors (processor) can be configured by software to perform certain operations as described herein. The device 100 can be a classic von Neumann computer architecture wherein instructions 124 are stored in non-volatile memory 106 and then loaded into a microprocessor 102. The volatile memory 104 can be used as temporary storage (i.e., a cache), to improve performance. Communication between the various subsystems in the device 100 is accomplished by a shared communications bus 108. In this example embodiment, the instructions 124 cause the microprocessor 102 to effect one or more aspects of the present invention. Examples of device 100 include devices 12, 14, 16, 18 and 22 in FIG. 3.

Data specific to one or more patients can be acquired either from network 20 via a network interface 120, or from sensors 122 attached to an analog-to-digital converter, or A/D converter 121. A user or operator may interact with the device 100 with a keyboard 112 or mouse 114, although those skilled in the art will appreciate that there are many other examples of devices for interacting with a computer, including touch-screen monitors, touchpads, trackballs, voice recognition software, etc. The output of the present invention may be conveyed to the user or operator on a display 110, or by causing an audio card 116 to make certain tones or sounds, or causing a digital-to-analog converter D/A converter 118 to signal an alarm, or by passing those results to other computers or devices on the network 20 via the network interface 120. Those skilled in the art will appreciate that there are other ways for a computer to communicate results to a user or operator, including printers, non-volatile memory devices, synthesized speech audio, etc.

Figure 5:
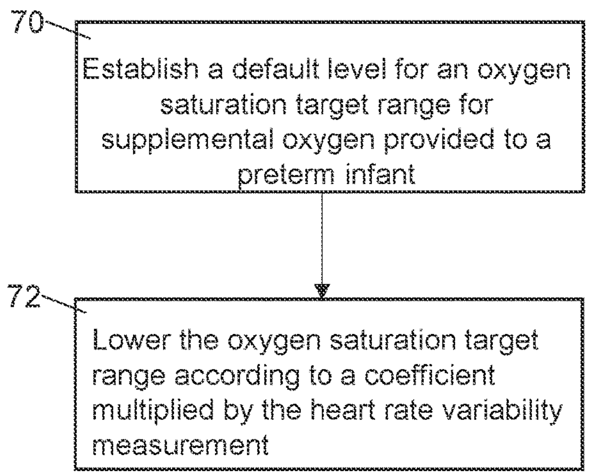
FIGS. 5 and 6 are flow diagrams illustrating exemplary methods in accordance with embodiments of the present disclosure.

With reference to FIG. 5, it will be appreciated that embodiments herein can establish a default level for an oxygen saturation range for supplemental oxygen provided to a preterm infant, as at 70. This default level is different from the adjusted oxygen saturation range as determined according to the processes described elsewhere herein. It will further be appreciated that adjusting the oxygen saturation range can be performed by lowering the oxygen saturation range according to a coefficient multiplied by the HRV measurement, as at 72. For example, the oxygen saturation target range may be equated to a default target range minus M times the PRM, where M is the coefficient. For example, the PRM may be calculated as 7 minus the highest HRCi over the previous 72 hours, the coefficient M might be selected as 0.5, and the default range might be 91-95%. Hence, the dynamic oxygen saturation target range for a particular patient might by 91 to 95%, minus 0.5×(7 minus the highest HRCi in the previous 72 hours).

Figure 6:
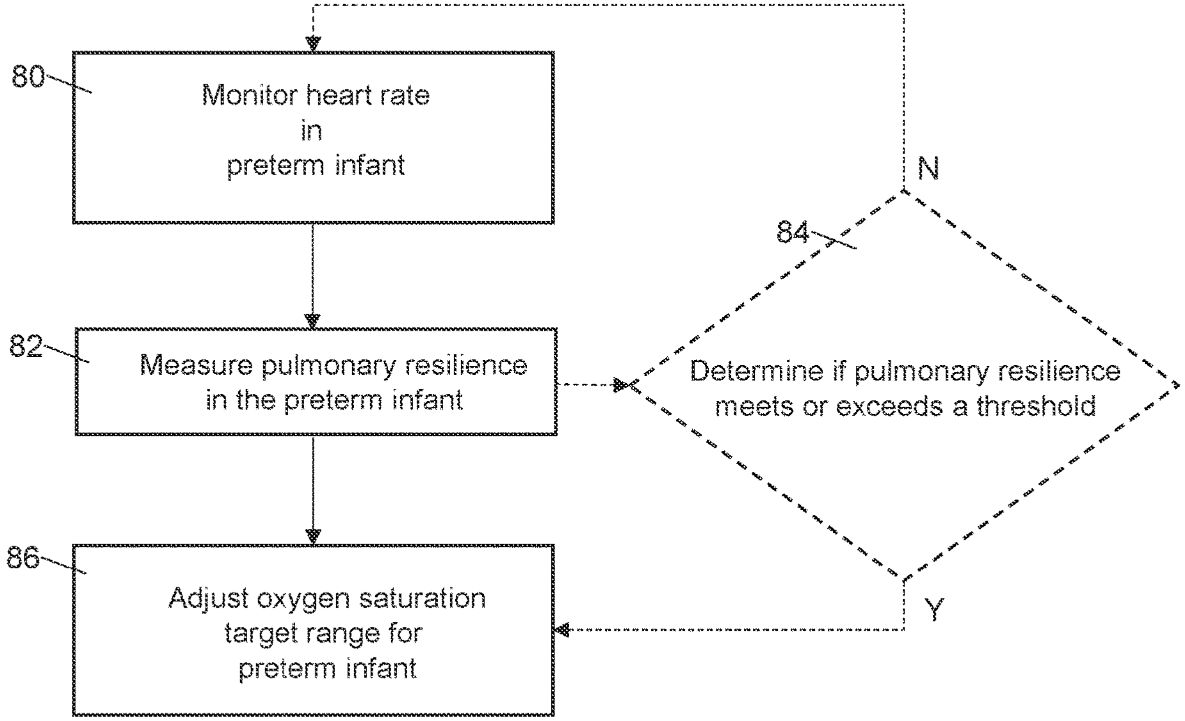

With reference to FIG. 6, another exemplary method according to the present disclosure dynamically targets oxygen saturation for preterm infants. As shown in FIG. 6, the method includes, as at 80, monitoring, via a monitoring device such as device 12 in FIG. 3, the heart rate in a preterm infant. As at 82, PRM in the preterm infant is determined. As at 86, an oxygen saturation target range for the preterm infant is adjusted. It will be appreciated that measuring the pulmonary resilience is or can be based on the HRV measurement as determined by the monitored heart rate. It will further be appreciated that adjusting the oxygen saturation target range is or can be based on the PRM. In various embodiments, the method can optionally determine if the PRM meets or exceeds a pre-established threshold, as at 84 and indicated in dashed lines. If the PRM does not meet or exceed a pre-established threshold, the method returns to 80. If the PRM meets or exceed a pre-established threshold, the method proceeds to 86.

In various embodiments, additional variables such as gestational age, birth weight, sex, maternal factors (e.g., race/ethnicity, antenatal steroid use, etc.), concomitant medications and interventions, and comorbidities, can be employed along with PRM measurements to assess oxygen saturation target range.

The present disclosure contemplates a variety of different systems each having one or more of a plurality of different features, attributes, or characteristics. A "system" as used herein can refer, for example, to various configurations of: (a) one or more monitoring or measurement devices; (b) one or more monitoring or measurement devices and one or more external computing devices; (c) one or more monitoring or measurement devices communicating via one or more networks; (d) one or more monitoring or measurement devices and one or more external computing devices communicating via one or more networks; and (e) one or more computing devices, such as desktop computers, laptop computers, tablet computers, personal digital assistants, mobile phones, and other mobile computing devices. It will be appreciated that the monitoring device can be programmed as to what to monitor or measure, how to report measurements, what parameters or thresholds are to be measured against and what trigger(s) to use in order to issue an alert. In various embodiments, the monitoring device 12 can measure heart rate, mean, median and standard deviation of heart rate, measures of heart rate decelerations and accelerations and heart rate entropy. Such programming can be performed prior to installation of the monitoring device or can be performed remotely by a computing device (e.g., 18) accessing the monitoring device (e.g., 12) over network 20. In various embodiments, an external system or device 22 may be accessed by the monitoring device 12 to obtain settings and/or updates to settings for establishing thresholds and/or making determinations in accordance with the present disclosure. External system/device 22 can be employed to facilitate centralized management of data, algorithms and thresholds as such items may be updated from time to time based on practice and statistical determinations, for example.

In various embodiments, one or more thresholds can be established for monitored conditions. When a measurement threshold is matched or exceeded, an alert can be generated. In various embodiments, alerts take the form of detected event communications indicating a met or exceeded threshold. The alert can provide a recommended course of action, for example. In various embodiments, the alert can provide instructions to an autonomous device to take instructed action.

As examples of the above, the device can be set to issue an alert in the form of a detected event communication when the received monitoring data exceeds a pre-established threshold for the device. The device can issue a detected event communication when the threshold is exceeded at a specific time, or over a set period of time, for example.

In various embodiments, the presently disclosed device and system can be connected to a cloud-based program where the generation and dissemination of alerts such as detected event communications is performed. A multitude of devices according to the present disclosure can be displayed on a map or building location such as a NICU to provide relative location on a building floor plan, for example. It will be appreciated that the monitoring device 12 can be securely configured and monitored via a cloud-based portal such as a system 22, which may be hosted by a third party, for example. Connections to the portal can be established via HTTPS, for example. Administrators can edit device settings, define sensor thresholds and create and edit event rules to trigger other applications and devices, for example. Account settings control groups, individual users and permissions to define who has access to the portal account. Multiple logins can be added to a single account, for example. An account can contain maps for multiple buildings or locations, so all devices can be managed through a single login.

In embodiments incorporating cloud-based operations and other embodiments, as described elsewhere herein, it will be appreciated that a processor need not be placed or secured within the monitoring device. For example, raw data collected via the monitoring device and/or system as described herein can be transmitted to a cloud-based portal (e.g., 22) and the processing and subsequent actions can thereby be performed remotely.

Thus, regardless of the location of the computing operations, the system can operate so as to receive data from one or more monitors or measuring devices, process the data such as by performing determinations, calculations and other analysis as described herein, assess whether an applied threshold has been met, and if a threshold has been met, trigger appropriate actions, such as alerts, communications and other actions as described herein. The system can further learn from and improve operations via a learning and/or neural network according to various embodiments.

In various embodiments, a display associated with a computing device such as 12, 14, 18, 22 can display event indicators if one or more defined thresholds is triggered.

In certain embodiments in which the system includes a computing device in combination with a measurement or monitoring device, the computing device is any suitable computing device (such as a server) that includes at least one processor and at least one memory device or data storage device. As further described herein, the computing device includes at least one processor configured to transmit and receive data or signals representing events, messages, commands, or any other suitable information between the computing device and the monitoring device. The processor of the computing device is configured to execute the events, messages, or commands represented by such data or signals in conjunction with the operation of the computing device. Moreover, the processor of the monitoring device is configured to transmit and receive data or signals representing events, messages, commands, or any other suitable information between the monitoring device and the computing device. The processor of the monitoring device is configured to execute the events, messages, or commands represented by such data or signals in conjunction with the operation of the monitoring device.

It will be appreciated that any combination of one or more computer readable media may be utilized. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing, including a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

As will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "circuit," "module," "component," or "system." Furthermore, aspects of the present disclosure may take the form of a computer program product embodied in one or more computer readable media having computer readable program code embodied thereon.

It will be appreciated that all of the disclosed methods and procedures herein can be implemented using one or more computer programs or components. These components may be provided as a series of computer instructions on any conventional computer-readable medium, including RAM, SATA DOM, or other storage media. The instructions may be configured to be executed by one or more processors which, when executing the series of computer instructions, performs or facilitates the performance of all or part of the disclosed methods and procedures.

Unless otherwise stated, devices or components of the present disclosure that are in communication with each other do not need to be in continuous communication with each other. Further, devices or components in communication with other devices or components can communicate directly or indirectly through one or more intermediate devices, components or other intermediaries. Further, descriptions of embodiments of the present disclosure herein wherein several devices and/or components are described as being in communication with one another does not imply that all such components are required, or that each of the disclosed components must communicate with every other component. In addition, while algorithms, process steps and/or method steps may be described in a sequential order, such approaches can be configured to work in different orders. In other words, any ordering of steps described herein does not, standing alone, dictate that the steps be performed in that order. The steps associated with methods and/or processes as described herein can be performed in any order practical. Additionally, some steps can be performed simultaneously or substantially simultaneously despite being described or implied as occurring non-simultaneously.

It will be appreciated that algorithms, method steps and process steps described herein can be implemented by appropriately programmed computers and computing devices, for example. In this regard, a processor (e.g., a microprocessor or controller device) receives instructions from a memory or like storage device that contains and/or stores the instructions, and the processor executes those instructions, thereby performing a process defined by those instructions. Furthermore, aspects of the present disclosure may take the form of a computer program product embodied in one or more computer readable media having computer readable program code embodied thereon.

Computer program code for carrying out operations for aspects of the present disclosure may be written in any combination of one or more programming languages, including an object oriented programming language such as Java, Scala, Smalltalk, Eiffel, JADE, Emerald, C++, C #, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on a user's computer, partly on a user's computer, as a stand-alone software package, partly on a user's computer and partly on a remote computer or entirely on the remote computer or server.

Where databases are described in the present disclosure, it will be appreciated that alternative database structures to those described, as well as other memory structures besides databases may be readily employed. The drawing figure representations and accompanying descriptions of any exemplary databases presented herein are illustrative and not restrictive arrangements for stored representations of data. Further, any exemplary entries of tables and parameter data represent example information only, and, despite any depiction of the databases as tables, other formats (including relational databases, object-based models and/or distributed databases) can be used to store, process and otherwise manipulate the data types described herein. Electronic storage can be local or remote storage, as will be understood to those skilled in the art. Appropriate encryption and other security methodologies can also be employed by the system of the present disclosure, as will be understood to one of ordinary skill in the art.

Although the present approach has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present approach.

The invention claimed is:

1. A method for dynamically targeting oxygen saturation for preterm infants, comprising:

monitoring, via a monitoring device, heart rate in a preterm infant to determine a heart rate variability measurement; and adjusting an oxygen saturation target range for the preterm infant, wherein the oxygen saturation target range is adjusted according to a coefficient multiplied by the heart rate variability measurement.

2. The method of claim 1, further comprising determining if the heart rate variability measurement meets or exceeds a pre-established threshold.

3. The method of claim 2, wherein the pre-established threshold is determined by:

determining a probability of one or more outcomes based on the heart rate variability measurement at both a low and a high oxygen saturation target range;

summing the product of a cost or a utility associated with each of the one or more outcomes, where each cost or each utility is weighted by the determined probability; and selecting the oxygen saturation target range that has a lower cost or a higher utility.

4. The method of claim 1, further comprising:

determining a probability of one or more outcomes based on the heart rate variability measurement at a continuum of oxygen saturation target ranges;

summing the product of a cost or a utility associated with each of the one or more outcomes, where each cost or each utility is weighted by the determined probability; and selecting the oxygen saturation target range that has the lowest cost or the highest utility.

5. The method of claim 1, further comprising establishing a default level for an oxygen saturation range for supplemental oxygen provided to the preterm infant, wherein the adjusted oxygen saturation target range is different from the default level.

6. The method of claim 5, wherein adjusting the oxygen saturation target range comprises lowering the oxygen saturation target range according to the coefficient.

7. The method of claim 1, further comprising re-adjusting the oxygen saturation target range at regular intervals based on the heart rate variability measurement.

8. The method of claim 1, further comprising issuing an alert regarding the adjusted oxygen saturation target range.

9. The method of claim 8, wherein the alert is issued to a servo-controlled oxygenation device operable to adjust oxygen flow to keep the preterm infant within the oxygen saturation target range.

10. A method for dynamically targeting oxygen saturation for preterm infants, comprising:

monitoring, via a monitoring device, heart rate in a preterm infant;

determining, via a computing device, a pulmonary resilience measurement in the preterm infant, wherein the pulmonary resilience measurement is based on a heart rate variability measurement determined based on the monitored heart rate; and adjusting an oxygen saturation target range for the preterm infant, wherein the oxygen saturation target range is adjusted according to a coefficient multiplied by the heart rate variability measurement.

11. The method of claim 10, wherein monitoring the heart rate comprises determining the heart rate variability measurement, and further comprising determining if the heart rate variability measurement meets or exceeds a pre-established threshold.

12. The method of claim 10, further comprising determining if the heart rate variability measurement meets or exceeds a pre-established threshold.

13. The method of claim 12, wherein the pre-established threshold is determined by:

determining a probability of one or more outcomes based on the pulmonary resilience measurement at both a low and a high oxygen saturation target range;

summing the product of a cost or a utility associated with each of the one or more outcomes, where each cost or each utility is weighted by the determined probability; and selecting the oxygen saturation target range that has a lower cost or a higher utility.

14. The method of claim 10, further comprising:

determining a probability of one or more outcomes based on the pulmonary resilience measurement at a continuum of oxygen saturation target ranges;

summing the product of a cost or a utility associated with each of the one or more outcomes, where each cost or each utility is weighted by the determined probability; and selecting the oxygen saturation target range that has the lowest cost or the highest utility.

15. The method of claim 10, further comprising establishing a default level for an oxygen saturation range for supplemental oxygen provided to a preterm infant, wherein the adjusted oxygen saturation target range is different from the default level.

16. The method of claim 15, wherein adjusting the oxygen saturation target range comprises lowering the oxygen saturation target range according to the coefficient multiplied.

17. The method of claim 10, further comprising re-adjusting the oxygen saturation target range at regular intervals based on the heart rate variability measurement and the pulmonary resilience measurement.

18. The method of claim 10, further comprising issuing an alert regarding the adjusted oxygen saturation target range.

19. The method of claim 18, wherein the alert is issued to a servo-controlled oxygenation device operable to adjust oxygen flow to keep the preterm infant within the oxygen saturation target range.

20. A system comprising:

a computing device comprising a processor and a memory storing instructions which, when executed by the processor, cause the processor to:

determine a heart rate variability measurement in the preterm infant based on a monitored heart rate;

determine an oxygen saturation target range for the preterm infant;

adjust the oxygen saturation target range according to a coefficient multiplied by the heart rate variability measurement; and issue an alert conveying the oxygen saturation target range for the preterm infant.

21. A method for dynamically targeting oxygen saturation for preterm infants, comprising:

monitoring, via a monitoring device, heart rate in a preterm infant to determine a heart rate variability measurement; and adjusting an oxygen saturation target range for the preterm infant, wherein adjusting the oxygen saturation target range is based on the heart rate variability measurement;

determining a probability of one or more outcomes based on the heart rate variability measurement at a continuum of oxygen saturation target ranges;

summing the product of a cost or a utility associated with each of the one or more outcomes, where each cost or each utility is weighted by the determined probability; and selecting the oxygen saturation target range that has the lowest cost or the highest utility.

22. A method for dynamically targeting oxygen saturation for preterm infants, comprising:

monitoring, via a monitoring device, heart rate in a preterm infant to determine a heart rate variability measurement;

adjusting an oxygen saturation target range for the preterm infant, wherein adjusting the oxygen saturation target range is based on the heart rate variability measurement; and determining if the heart rate variability measurement meets or exceeds a pre-established threshold, wherein the pre-established threshold is determined by:

determining a probability of one or more outcomes based on the heart rate variability measurement at both a low and a high oxygen saturation target range;

summing the product of a cost or a utility associated with each of the one or more outcomes, where each cost or each utility is weighted by the determined probability; and selecting the oxygen saturation target range that has a lower cost or a higher utility.

23. A method for dynamically targeting oxygen saturation for preterm infants, comprising:

monitoring, via a monitoring device, heart rate in a preterm infant;

determining, via a computing device, a pulmonary resilience measurement in the preterm infant, wherein the pulmonary resilience measurement is based on a heart rate variability measurement determined based on the monitored heart rate;

adjusting an oxygen saturation target range for the preterm infant, wherein adjusting the oxygen saturation target range is based on the pulmonary resilience measurement, determining a probability of one or more outcomes based on the pulmonary resilience measurement at a continuum of oxygen saturation target ranges;

summing the product of a cost or a utility associated with each of the one or more outcomes, where each cost or each utility is weighted by the determined probability; and selecting the oxygen saturation target range that has the lowest cost or the highest utility.

24. A method for dynamically targeting oxygen saturation for preterm infants, comprising:

monitoring, via a monitoring device, heart rate in a preterm infant;

determining, via a computing device, a pulmonary resilience measurement in the preterm infant, wherein the pulmonary resilience measurement is based on a heart rate variability measurement determined based on the monitored heart rate;

adjusting an oxygen saturation target range for the preterm infant, wherein adjusting the oxygen saturation target range is based on the pulmonary resilience measurement; and determining if the pulmonary resilience measurement meets or exceeds a pre-established threshold, wherein the pre-established threshold is determined by:

determining a probability of one or more outcomes based on the pulmonary resilience measurement at both a low and a high oxygen saturation target range;

summing the product of a cost or a utility associated with each of the one or more outcomes, where each cost or each utility is weighted by the determined probability; and selecting the oxygen saturation target range that has a lower cost or a higher utility.

25. A system comprising:

a computing device comprising a processor and a memory storing instructions which, when executed by the processor, cause the processor to:

determine a heart rate variability measurement in the preterm infant based on a monitored heart rate;

determine a probability of one or more outcomes based on the heart rate variability measurement at a continuum of oxygen saturation target ranges;

sum the product of a cost or a utility associated with each of the one or more outcomes, where each cost or each utility is weighted by the determined probability;

select an oxygen saturation target range that has the lowest cost or the highest utility; and issue an alert conveying the oxygen saturation target range for the preterm infant.

26. A system comprising:

a computing device comprising a processor and a memory storing instructions which, when executed by the processor, cause the processor to:

determine a heart rate variability measurement in the preterm infant based on a monitored heart rate;

determine if the heart rate variability measurement meets or exceeds a pre-established threshold, wherein the pre-established threshold is determined by:

determining a probability of one or more outcomes based on the heart rate variability measurement at both a low and a high oxygen saturation target range;

summing the product of a cost or a utility associated with each of the one or more outcomes, where each cost or each utility is weighted by the determined probability; and selecting an oxygen saturation target range that has a lower cost or a higher utility; and issue an alert conveying the oxygen saturation target range for the preterm infant.

* * * * *